United States Patent [19]

Takaya et al.

[11] Patent Number: 4,656,160

[45] Date of Patent: * Apr. 7, 1987

[54] AMINOGLYCOSIDE DERIVATIVES

[75] Inventors: Takao Takaya, Kawanishi; Nobuyoshi Yasuda, Nishinomiya; Hideo Tsutsumi, Yuhigaoka; Keiji Matsuda, Takatsuki, all of Japan

[73] Assignee: Fujisawa Pharmaceutical Co., Ltd., Osaka, Japan

[*] Notice: The portion of the term of this patent subsequent to Jan. 15, 2001 has been disclaimed.

[21] Appl. No.: 799,110

[22] Filed: Nov. 18, 1985

[30] Foreign Application Priority Data

Nov. 29, 1984 [JP] Japan .................. 59-253720

[51] Int. Cl.$^4$ .................. A61K 31/71; C07H 15/234
[52] U.S. Cl. .................. 514/41; 514/40; 536/13.7; 536/13.8; 536/16.8
[58] Field of Search .................. 536/13.7, 13.8, 16.8; 514/41, 40

[56] References Cited

U.S. PATENT DOCUMENTS

| | | | |
|---|---|---|---|
| 4,298,727 | 11/1981 | Umezawa et al. | 536/13.7 |
| 4,332,794 | 1/1982 | Umezawa et al. | 536/13.7 |
| 4,493,831 | 1/1985 | Takaya et al. | 536/13.7 |
| 4,547,492 | 10/1985 | Umezawa et al. | 536/13.7 |

Primary Examiner—Johnnie R. Brown
Attorney, Agent, or Firm—Oblon, Fisher, Spivak, McClelland & Maier

[57] ABSTRACT

Aminoglycoside derivatives and pharmaceutically acceptable salts thereof which are useful as prophylactic and therapeutic agents for infectious diseases caused by pathogenic microorganisms, and a pharmaceutical composition comprising the same.

5 Claims, No Drawings

AMINOGLYCOSIDE DERIVATIVES

This invention relates to new aminoglycoside derivatives and pharmaceutically acceptable salts thereof. More particularly, it relates to new aminoglycoside derivatives and pharmaceutically acceptable salts thereof which have antiviral activity, and immunostimulating activity, processes for the preparation thereof and a pharmaceutical composition comprising the same.

Accordingly, it is an object of this invention to provide new aminoglycoside derivatives which are useful as prophylactic and therapeutic agents for infectious diseases caused by pathogenic microorganisms.

Another object of this invention is to provide processes for preparing the aminoglycoside derivatives.

Further object of this invention is to provide a pharmaceutical composition comprising the aminoglycoside derivatives.

The object new aminoglycoside derivatives of this invention can be represented by the following formula:

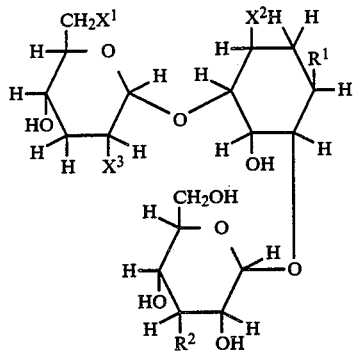

(I)

wherein
R$^1$ is higher alkanoylamino,
R$^2$ is amino or protected amino, and
X$^1$, X$^2$ and X$^3$ are each amino or acylamino, and pharmaceutically acceptable salts thereof.

According to this invention, the new aminoglycoside derivatives (I) can be prepared by, for example, the following processes.

Process 1:

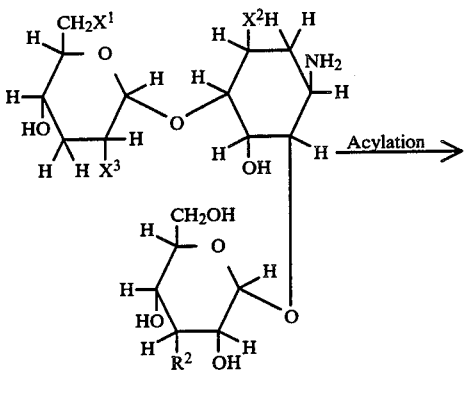

(II)

or its reactive
derivative at
the amino group
or a salt thereof

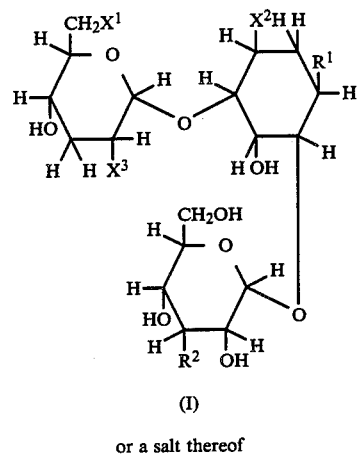

(I)

or a salt thereof

Process 2:

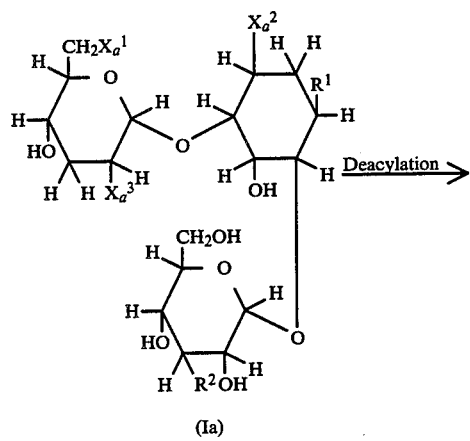

(Ia)

or a salt thereof

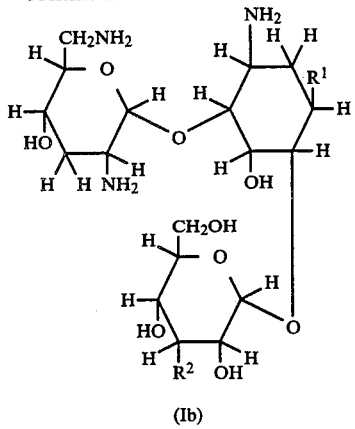

(Ib)

or a salt thereof wherein
$R^1$, $R^2$, $X^1$, $X^2$ and $X^3$ are each as defined above, and $X_a^1$, $X_a^2$ and $X_a^3$ are each acylamino.

Suitable pharmaceutically acceptable salts of aminoglycoside derivatives (I), (Ia) and (Ib) and salt of the starting compound (II) are conventional salts and may include an organic or inorganic acid addition salt such as hydrochloride, hydrobromide, hydroiodide, sulfate, nitrate, carbonate, phosphate, acetate, fumarate, maleate, tartrate, methanesulfonate, benzenesulfonate, toluenesulfonate, and the like.

In the above and subsequent descriptions of this specification, suitable examples and illustrations of the various definitions are explained in detail in the following.

The term "lower" is intended to mean 1 to 6 carbon atom(s), unless otherwise provided.

"Protected amino" means an amino group protected by one or two conventional amino-protective group such as an acyl as mentioned below, and particularly suitable examples of the acyl group may be, for example, lower alkoxycarbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, etc.), ar(lower)alkoxycarbonyl preferably phenyl(lower)alkoxycarbonyl which may have nitro or lower alkoxy (e.g. benzyloxycarbonyl, p-nitrobenzyloxycarbonyl, p-methoxybenzyloxycarbonyl, etc.), lower alkanoyl (e.g. formyl, acetyl, etc.), ar(lower)alkylidene (e.g. salicylidene, etc.), ar(lower)alkyl which may have nitro (e.g. benzyl, p-nitrobenzyl, benzhydryl, trityl, etc.), or the like.

Suitable "acyl" moiety in the terms "acylamino" may include carbamoyl, an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$-$C_7$)-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, etc.), halogen (e.g. chloride, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, acylamino, aryloxy (e.g., benzyloxy, tolyloxy, etc.), lower alkanoyloxy (e.g. formyloxy, acetyloxy, propionyloxy, butyryloxy, isobutyryloxy, valeryloxy, isovaleryloxy, pivaloyloxy, hexanoyloxy, etc.), and the like, and the preferable acyl having such substituent(s) may be mono (or di or tri) halo(lower)alkanoyl (e.g., chloroacetyl, bromoacetyl, dichloroacetyl, trifluoroacetyl, etc.), amino(lower)alkanoyl (e.g., glycyl, aminopropionyl, diaminobutyryl, etc.), phenyl(lower)alkoxycarbonylamino(lower)alkanoyl (e.g., benzyloxycarbonylglycyl, etc.), phenyl(lower)alkoxycarbonylcarbamoyl (e.g., benzyloxycarbonylcarbamoyl, etc.), phenyl(lower)alkoxy(lower)alkanoyl (e.g., benzyloxyacetyl, benzyloxypropionyl, etc.), carboxy(lower)alkanoyl (e.g., carboxyacetyl, carboxypropionyl, etc.), hydroxy(lower)alkanoyl (e.g. glycoloyl, hydroxypropionyl, etc.), etc.

Suitable "higher alkanoyl" moiety in the term "higher alkanoylamino" may be the ones having 8 or more carbon atoms such as octanoyl, nonanoyl, decanoyl, undecanoyl, lauroyl, myristoyl, pentadecanoyl, palmitoyl, heptadecanoyl, stearoyl, icosanoyl, docosanoyl, tetracosanoyl, or the like, preferably ones having 8 to 24 carbon atoms.

The processes for preparing the object compounds of the present invention are explained in detail in the following.

Process 1

The object compound (I) or a salt thereof can be prepared by subjecting the compound (II) or its reactive derivative at the amino group or a salt thereof to acylation reaction.

This acylation reaction can be conducted by reacting the compound (II) or its reactive derivative at the amino group or a salt thereof with an acylating agent.

Suitable reactive derivative at the amino group of the compound (II) may include silyl derivative formed by the reaction of the compound (II) with a silyl compound such as bis(trimethylsilyl)acetamide, mono(trimethylsilyl)acetamide or the like; and the like.

Suitable acylating agent may include conventional one and can be shown by the formula: $R_a^1$—OH (III)

(wherein $R_a{}^1$ higher alkanoyl) or its reactive derivative at the carboxy group or a salt thereof.

Suitable salt of the compounds (III) may include a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction can preferably be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

When the acylating agent is used in a form of free acid, the reaction of this process may preferably be conducted in the presence of a condensing agent such as carbodiimidic compound (e.g. N,N'-carbonyldiimidazole, N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride, 2,2,4,4,6,6-hexachloro-1,3,5,2,4,6-triazatriphosphorine, 1-benzenesulphonyloxy-6-chloro-1H-benzotriazole, p-toluenesulfonyl chloride, isopropoxybenzenesulfonyl chloride, or a mixed condensing agent such as triphenylphosphine and a carbon tetrahalide (e.g. carbon tetrachloride, carbon tetrabromide, etc.) or so-called Vilsmeier reagent (e.g. a complex of N,N-dimethylformamide with phosphoryl chloride, phosgene or thionyl chloride).

The reaction is usually conducted in a conventional solvent which does not adversely influence the reaction such as water, acetone, dioxane, acetonitrile, ethyl acetate, N,N-dimethylformamide, dimethylsulfoxide, tetrahydrofuran, dichloromethane, chloroform, pyridine, N-methylmorpholine, N-methylpyrrolidine, etc. or a mixture thereof.

The reaction temperature is not critical and this reaction can be conducted within the temperature range of cooling to heating.

In the present acylation reaction, other amino group(s) may be similarly acylated during the reaction or the post-treatment of the present reaction, which is also included within the scope of the present reaction.

Process 2

The object compound (Ib) or a salt thereof can be prepared by subjecting the compound (Ia) or a salt thereof to deacylation reaction.

The present deacylation reaction is carried out in accordance with a conventional method such as hydrolysis; reduction; deacylation using Lewis acid; deacylation method by reacting the compound (Ia) with iminohalogenating agent and then with iminoetherifying agent, and, if necessary, subjecting the resulting compound to hydrolysis; or the like.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like.

The reaction temperature is not critical, and the reaction is usually carried out under cooling or at ambient temperature.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitable selected in accordance with the kind of the protective group of the amino group and the elimination method as mentioned above, and the present reaction is preferably carried out under a mild condition such as under cooling, at ambient temperature or slightly elevated temperature.

The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.), catalytic reduction using conventional catalyst and the like.

The reaction temperature is not critical, and the reaction is usually carried out under cooling to warming. In the present deacylation, other acylamino group(s) may be similarly deacylated during the reaction or the post-treatment of the present reaction, which is also included within the scope of the present reaction.

The object compound (I) and pharmaceutically acceptable salts thereof have antiviral activity and immuno-stimulating activity and therefore, are useful as an antiviral agent and a prophylactic agent for infectious diseases caused by pathogenic microorganisms for human being, animals and plants.

For prophylacetic or therapeutic administration, the object compound (I) and the pharmaceutically acceptable salts thereof of the present invention are used in the form of conventional pharmaceutical preparation comprising the same, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule or liquid form such as solution, suspension, syrup, emulsion, lemonade and the like. If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethylene glycol and the like.

While the dosage of the compound (I) or pharmaceutically acceptable salts thereof may vary from and also depend upon the age, conditions of the patient, kinds of diseases, kinds of the compound (I) or pharmaceutically acceptable salts thereof to be applied, etc. In general, preferable dosage of the compound (I) or pharmaceutically acceptable salts thereof to the patient can be selected from 0.1-100 mg/kg/day.

The following Examples are given for the purpose of illustrating this invention. In the Examples, it is to be noted that numbering of carbon atom's position of aminoglycoside derivatives is given in accordance with those of tobramycin as illustrated as follows.

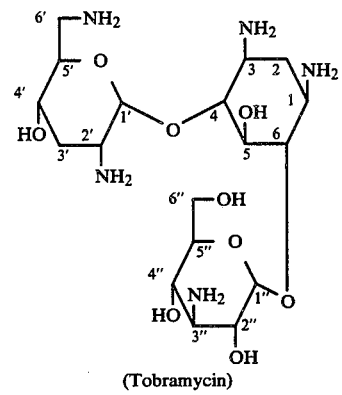

(Tobramycin)

In order to illustrate the usefulness of the object compound, anti-viral activity and cytotoxicity of a representative compound of the present invention are shown below.

Assays were carried out in confluent Vero cell cultures in multi-well trays (96 wells). The cell cultures were grown to confluence in Eagle's minimal essential medium (MEM) supplemented with 5% fetal bovine serum (FBS).

(1) Anti-HSV (herpes simplex virus) activity (A) Test Method

The culture medium was changed to 0.5% FBS-MEM. The cell cultures were inoculated with about 100 TCID$_{50}$ of HSV-I Miyama strain, and immediately thereafter, exposed to varying concentrations of the test compound and incubated for 2 days at 37° C. in humidified 5% CO$_2$-95% air. 4 wells were used in each concentrations. They were fixed with 5% trichloroacetic acid and stained with 0.1% crystalviolet. The viral CPE was observed microscopically (x40). Antiviral activity was expressed as ID$_{50}$ (50% inhibitory dose), that is, the concentration of compound required to reduce viral CPE by 50% (within the well), when it had reached completion (100% cell destruction) in the control virus-infected cell cultures.

(B) Test Compound

1-N-palmitoyl-3''-N-trifluoroacetyltobramycin trihydrochloride.

(C) Test Result

| Anti-HSV activity (μg/ml) |
| --- |
| 4.4 |

EXAMPLE 1

To a solution of 3,2',6'-tris-N-benzyloxYoarbonyl-3"-N-trifluoroacetyltobramycin (0.67 g) in a mixture of tetrahydrofuran (30 ml) and water (6 ml) was dropwise added palmitoyl chloride (0.2 g) under ice-cooling, keeping the pH 8-9 with triethylamine. The mixture was stirred for an hour at the same condition. The reaction mixture was concentrated under reduced pressure to give a solid. The solid was washed with 1N-hydrochloric acid, ethyl ether, isopropyl alcohol, and water, respectively, and dried over phosphorus pentoxide in vacuo to give 3,2',6'-tris-N-benzyloxycarbonyl-1-N-palmitoyl-3"-N-trifluoroacetyltobramycin (0.75 g).

mp : 284°-286° C.

IR (Nujol) : 3350-3300, 1710-1690, 1540, 1290, 1170 cm$^{-1}$.

NMR (DMSO-d$_6$, δ) : 0.85-1.03 (3H, m), 1.25 (26H, s), 1.50-1.80 (2H, m), 1.75-2.30 (4H, m), 4.85-5.20 (6H, m), 7.31 (5H, s), 7.35 (10H, s).

EXAMPLE 2

A solution of 3,2',6'-tris-N-benzyloxycarbonyl-1-N-palmitoyl-3"-N-trifluoroacetyltobramycin (0.70 g) in a mixture of methanol (15 ml) and conc. hydrochloric acid (0.1 ml) was hydrogenated under 1 atmospheric pressure of hydrogen in the presence of 10% palladium on carbon (0.4 g) at ambient temperature for 6 hours. The reaction mixture was concentrated under reduced pressure and dissolved in a mixture of water (10 ml) and methanol. The solution was evaporated in vacuo to give a residue. The residue was dissolved in water (30 ml) and lyophilized to give 1-N-palmitoyl-3"-N-trifluoroacetyltobramycin trihydrochloride (0.34 g) as a solid.

mp : >224° C. (dec.).

$[\alpha]_D^{20}$: +58.7° (C1.0 H$_2$O).

IR (Nujol) : 3350-3200, 1710, 1645-1620, 1165, 1030 cm$^{-1}$.

NMR (CD$_3$OD, δ) : 0.80-0.97 (3H, m), 1.28 (26H, s), 1.90-2.50 (6H, m), 5.10 (1H, d, J=3Hz), 5.90 (1H, d, J=3.5Hz).

FD Mass : 824 (M$^+$+22), 802(M$^+$), 728 (M$^+$-74).

What we claim is:

1. Aminoglycoside derivatives of the formula :

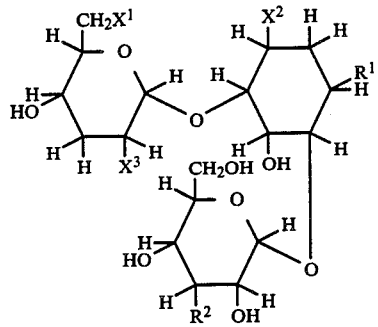

wherein

R$^1$ is C$_{8-24}$ alkanoylamino,

R$^2$ is amino or protected amino, and

X$^1$, X$^2$ and X$^3$ are each amino or acylamino, and pharmaceutically acceptable salts thereof.

2. The compound of claim 1, wherein R$^1$ is palmitoylamino.

3. The compound of claim 2, which is 1-N-palmitoyl-3"-N-trifluoroacetyltobramycin trihydrochloride.

4. A pharmaceutical composition comprising an antiviral effective amount of the aminoglycoside of claim 1 or pharmaceutically acceptable salt thereof in association with a pharmaceutically acceptable, substantially non-toxic carrier or excipient.

5. A method for treating herpes simplex virus comprising administering an antiviral effective amount of the aminoglycoside of claim 1 to a host in need of such treatment.

* * * * *